US006758804B2

(12) United States Patent
Anderson

(10) Patent No.: US 6,758,804 B2
(45) Date of Patent: Jul. 6, 2004

(54) METHOD AND APPARATUS FOR UNLOADING GRADIENTS

(75) Inventor: Norman G. Anderson, Rockville, MD (US)

(73) Assignee: Large Scale Proteomics, Vacaville, CA (US)

( * ) Notice: Subject to any disclaimer, the term of this patent is extended or adjusted under 35 U.S.C. 154(b) by 290 days.

(21) Appl. No.: 09/915,291

(22) Filed: Jul. 27, 2001

(65) Prior Publication Data

US 2002/0023884 A1 Feb. 28, 2002

Related U.S. Application Data

(63) Continuation-in-part of application No. 09/628,340, filed on Jul. 28, 2000.

(51) Int. Cl.[7] ................................................. B04B 11/08
(52) U.S. Cl. .......................... 494/37; 210/789; 210/513
(58) Field of Search ..................... 494/37, 85; 210/787, 210/513–516, 518, 789; 422/72, 101

(56) References Cited

U.S. PATENT DOCUMENTS

| | | | | |
|---|---|---|---|---|
| 593,333 | A | * 11/1897 | Park | 210/518 |
| 1,240,360 | A | * 9/1917 | Palmer | 210/516 |
| 3,981,804 | A | 9/1976 | Gigliello | |
| 4,001,122 | A | * 1/1977 | Griffin | 210/516 |
| 4,279,863 | A | * 7/1981 | Friehler | 422/102 |
| 4,346,608 | A | 8/1982 | Olenick | |
| 4,828,716 | A | * 5/1989 | McEwen et al. | 210/740 |
| 4,917,801 | A | 4/1990 | Luderer | |
| 5,474,687 | A | * 12/1995 | Van Vlasselaer | 210/782 |
| 5,840,502 | A | * 11/1998 | Van Vlasselaer | 435/7.21 |

OTHER PUBLICATIONS

Anderson et al., *Analytical Techniques for Cell Fractions: VII, A Simple Gradient–Forming Apparatus*, Anal Biochem (1967) 21:259–265.
Atherton et al., *Chromatography and Zonal Centrifugations: Predictions of the Optimum Initial Chamber Compositions of a Multichambered Concentration and Density Gradient Device*, Anal Biochem (1972), 49:326–335.
Ayad et al., *A Simple Method for the Production of Accurate Linear Gradients Using a Constant–Speed Peristaltic Pump*. Anal Biochem (1968) 22:533–535.
Birnie et al., *A Simple Density–Gradient Engine for Loading Large–Capacity Zonal Ultracentrifuge Rotors*. Anal Biochem (1968) 22:171–174.
Clark et al., *Hydrostatically Balanced Gradient–Formers: Programming of Gradients*. Anal Biochem (1980) 103:94–100.
Coombs et al., *Generating Sucrose Gradients in Three Minutes by Tilted Tube Rotation*. Anal Biochem (1985) 148:254–259.
Corless JM., *Simple and Inexpensive Fabrication of Small–Volume Density Gradients*. Anal Biochem (1978) 84:251–255.
Gordon et al., *A Simple Design of an Apparatus for the Generation of Sucrose Gradients for Large–Scale Zonal Separation of Ribosomal Subunits*, Anal Biochem (1977) 83:763–766.

(List continued on next page.)

Primary Examiner—Tony G. Soohoo
Assistant Examiner—David Sorkin
(74) Attorney, Agent, or Firm—John C. Robbins; John E. Tarcza

(57) ABSTRACT

Devices and methods for removing portions of gradients relate to a float with an upper concave surface for collecting the gradient portion.

4 Claims, 17 Drawing Sheets

OTHER PUBLICATIONS

Gropper et al., *Band–Forming Caps for the Layering of Sample in Swinging–Bucket Rotors.* Anal Biochem (1966) 16:171–176.

Henderson AR., *A Constant–Volume Device for Preparing Isokinetic Sucrose Density Gradients.* Anal Biochem (1969) 27:315–318.

Hopkins TR., *Another Density Gradient Fractionator.* Anal Biochem (1973) 53:339–341.

Lange et al., *A Semiautomated System for the Production and Analysis of Sucrose Density Gradients.* Anal Biochem (1974) 59:129–145.

Leif RC., *Density Gradient System: I. Formation and Fractionation of Density Gradients.* Anal Biochem (1968) 25:271–282.

Liedtke et al., *An Apparatus for Density Gradient Forming and Nonpuncturing Fractionation.* Anal Biochem (1974) 62:377–385.

Luthe DS., *A Simple Technique for the Preparation and Storage of Sucrose Gradients.* Anal Biochem (1983) 135:230–232.

Margolis J., *A Versatile Gradient–Generating Device.* Anal Biochem (1969) 27:319–322.

McRee D., *Inexpensive Apparatus for Preparation of Multiple Discontinuous Gradient.* Anal Biochem (1978) 87:648–652.

Neff et al., *A Modified Fixed–Volume Mixer for Extended Sucrose Density Gradients.* Anal Biochem (1971) 41:363–371.

Olenick et al., *A Floating Device to Permit Fractionation of Density Gradients From the Top.* Anal Biochem (1979) 97:72–76.

Samis HV., *A Simple Density Gradient Generator.* Anal Biochem (1966) 15:355–357.

Sartory et al., *Design of a Generalized n–Solute Mixing–Chamber Gradient Generator.* Anal Biochem (1978) 88:539–551.

Shearer G., *A Syringe–Based Gradient Former for Linear and Exponential Gradients.* Anal Biochem (1994) 221:397–400.

Sheeler et al., *Method and Apparatus for Producing and Collecting a Multiplicity of Density Gradients.* Anal Biochem (1978) 87:612–621.

Siakotos et al., *New Loading System for Preparing Density Gradients for Swinging–Bucket Rotors Using Programmed Gradient Pumps.* Anal Biochem (1971) 43:32–41.

Wallach DFH., *A Simple System for Rapid Generation of Duplicate Density Gradients.* Anal Biochem (1970) 37:138–141.

\* cited by examiner

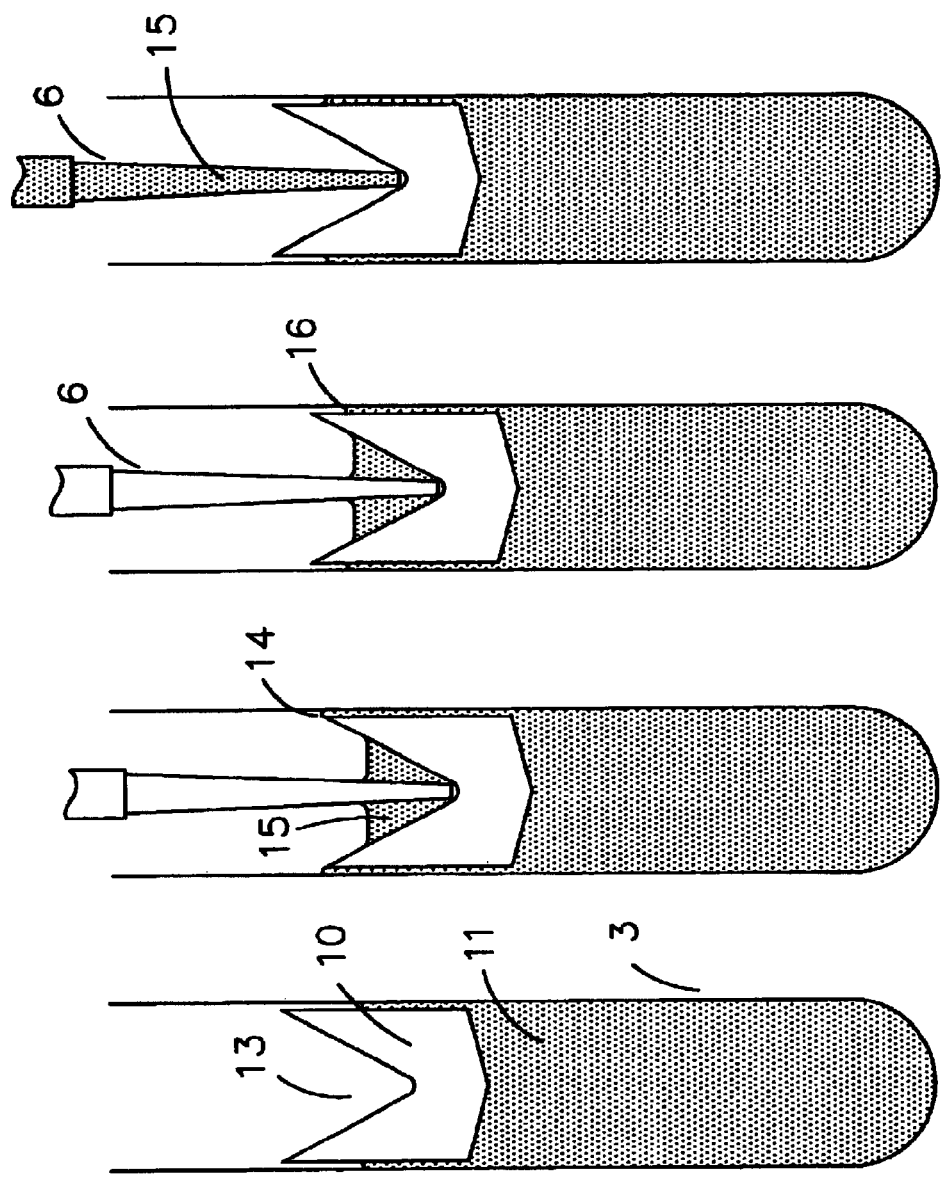

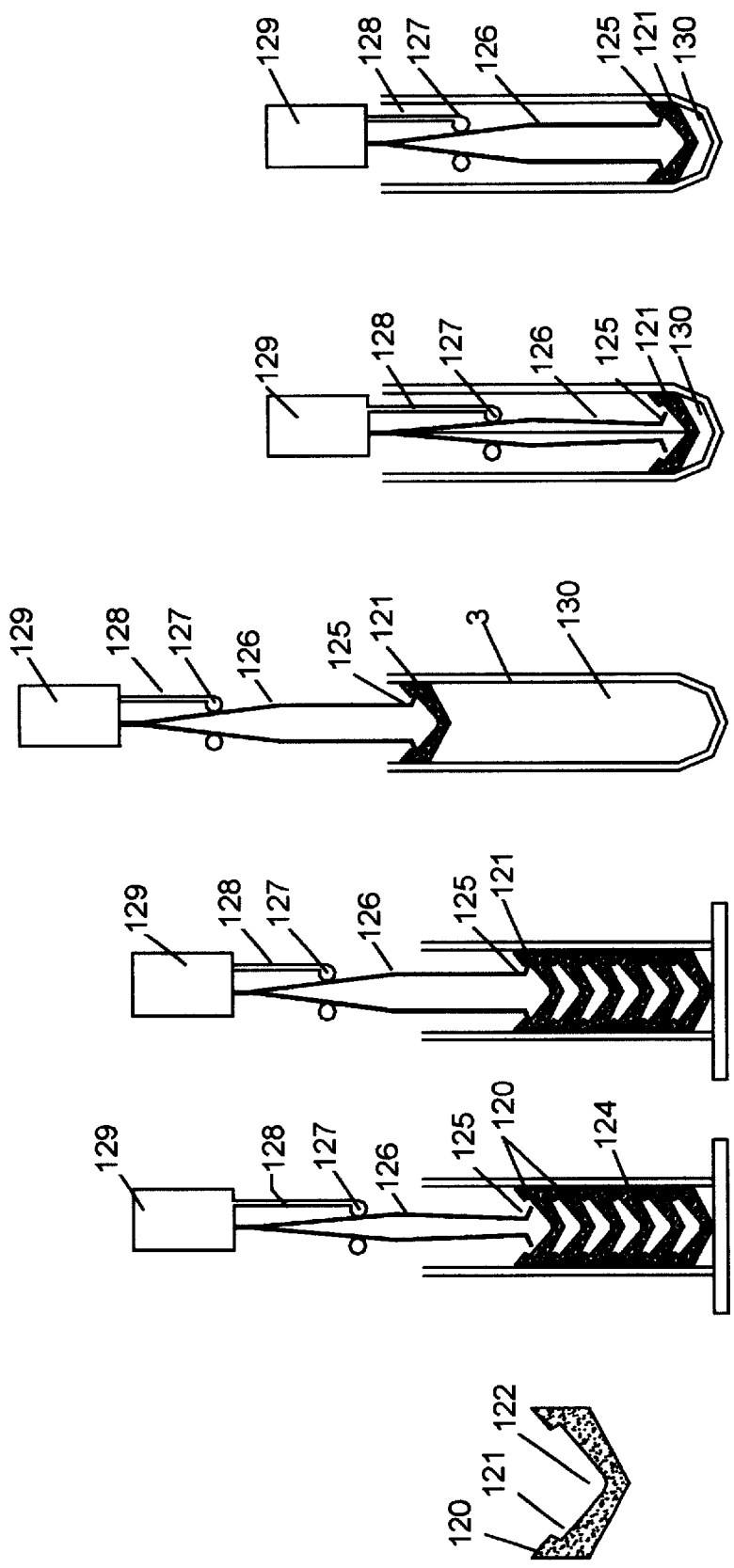

METHOD AND APPARATUS FOR UNLOADING GRADIENTS

This application is a CIP of U.S. patent application Ser. No. 09/628,340, filed Jul. 28, 2000.

BACKGROUND OF THE INVENTION

A. Field of the Invention

The present invention relates to a method and apparatus for separating portions of liquid in a vessel. Specifically, the invention relates to a method and apparatus for separating portions of a liquid density gradient where layers or zones of materials are produced during the course of centrifugal separation of cellular and/or subcellular material. The present invention is applicable to cell separation and subcellular fractionation and analysis, and to density gradient methods used in molecular biology, in polymer chemistry, in physical chemistry, and in the characterization of physical particles generally. The present invention further relates to an automated method and apparatus for recovering fractions from multiple density gradients in parallel using floats that float on the surface of the gradient.

B. Description of the Related Art

The publications and other materials used herein to illuminate the background of the invention and to provide details respecting the practice are incorporated herein by reference, and for convenience are respectively grouped in the appended List of References and are incorporated by reference in their entirety.

Density gradient centrifugation has been used to separate biological particles on the basis of, for instance, sedimentation rate or banding density. Continuous gradients may be formed either using simple manual techniques, or by using gradient formers, of which a variety have been described (Boch and Ling). In other methods, step gradients may be made initially, and used directly in simplified procedures, or they may be linearized by diffusion, or mechanically by slowly turning the tubes in an angled position. Samples of material, such as cellular material, are placed in a centrifuge tube above such a gradient, subjected to centrifuging in a centrifuge for a predetermined time period and then removed from the centrifuge. The centrifuging causes specific portions or fractions of the cellular material to move to specific portions of the gradient.

If dyes or other observable indicators are present, visual inspection may reveal separate zones or layers of material. The various zones or layers may also be made visible by scattered or reflected light, by light absorbance, or by fluorescence to guide recovery. Once identification of separations is made, one or more zones or fractions of the gradient may be removed for further analysis. Gradients may be removed or recovered by pumping the desired portion of the gradient out of the centrifuge tube through a small tube extending to the bottom of the centrifuge tube. Alternatively, the gradients can be removed by displacing the gradient with a denser fluid introduced to the bottom, with the gradient then collected through a tight-fitting inverted funnel at the top. The gradient may pass through a flow cell in a calorimeter, spectrophotometer, turbidometer or fluorometer to determine the location of particle bands. The simplest method for collecting a gradient is by puncturing a hole in the bottom of a plastic centrifuge tube, and allowing the gradient to drip out, in which case, the drops may be collected individually or in groups.

In zonal centrifuges, gradients are unloaded while the rotor is spinning, and centrifugal force maintains the order of zones. This technique is not readily adaptable to recovering gradients from individual centrifuge tubes.

To attain reproducible precision rate zonal centrifugation or precision isopycnic centrifugation done in multiple-parallel gradients, gradients must be unloaded in a consistent identical manner, with as little loss of resolution as possible. Current unloading methods do not provide a reliable means for processing large numbers of gradients in a reliable, reproducible manner. Therefore, there is a need for a simple method for unloading identical gradients, and for recovering from them identical fractions.

SUMMARY OF THE INVENTION

One object of the present invention is to provide a simple and reliable means for unloading individual layers or zones from liquid density gradients.

In accordance with one aspect of the present invention, a float is formed with a concave upper surface thereby defining a well. The float is adapted for insertion into a vessel such as a centrifuge tube having a density gradient therein. The float may be pushed downward in the tube to allow a portion of the density gradient to spill over an upper edge of the float, thereby allowing a desired portion of the density gradient to spill over into the well. A pipetter may then be used to remove the separated portion of the density gradient now located in the well. By repeatedly pushing the float successively lower into the tube, various portions of the density gradient may be easily separated and removed.

The float of the present invention may be used in any of a variety of applications. For instance, the float may be used in manually conducted separation procedures where a technician manually pushes the float down in order to capture a portion of a gradient in the well, then remove the separated portion of the gradient with a pipetter or syringe.

The float of the present invention may form part of an automated system where a remote controlled pipetter is lowered into a tube to both push the float down, and to capture a portion of a gradient. The automated system may include an optical reader to identify zones or layers of the gradient in the tube in order to determine the movement of the float necessary to capture a desired portion of the gradient. Alternatively, the automated system may be programmed to lower the float to a predetermined depth thereby capturing a predetermined portion of a gradient for removal.

The float of the present invention may also form part of an automated system in which samples isolated by the float are expelled from the centrifuge by brief application of air pressure. In this version the pipette tube is stationary, and the centrifuge tube, float, an airtight cap and means for holding the cap in place comprise a unit which is moved vertically at suitable intervals by a stepping motor. The stationary pipette enters the cap through a small O-ring. Tubular means for conduction of air under pressure through the cap are provided, together with means for moving a series of collecting tubes to receive the expelled fractions.

The float of the present invention and the automated fractionation and recovery systems may further be reduplicated to form an array of recovery systems such that a set of identical or comparable gradients may be unloaded in parallel.

The float of the present invention may also be modified through the inclusion of a circumferential groove in the upper cavity of the float so that it may be easily grasped by a gripper which can serve to insert the float before centrifugation, and remove it after the gradient zones have been recovered.

A float of the instant invention can be configured of a particular material or of particular materials so to have a particular density. That also can be achieved by having particular coatings on the float, having the float contain a ballast, by having a hollow float containing a material or materials of particular density and so on. Moreover, the float need not be a solid but can be perforated, for example by a tube or tubes, or can be porous to enable passage of fluids therethrough.

BRIEF DESCRIPTION OF THE DRAWINGS

FIGS. 2A, 2B, 2C and 2D are further side views showing operations of removal of a gradient layer from a vessel using a second embodiment of a push-down float in combination with a pipetter, the second embodiment of the push-down float having an enlarged center collecting well;

FIG. 10 illustrates a grooved recovery float and gripper for inserting and recovering floats.

FIG. 12A thus is a float similar to that depicted in FIGS. 12A–12D. However, the entire float of FIG. 12A could be made of a permeable material. FIG. 12B depicts essentially a solid ring and side wall structure with a permeable flat disc in the center. FIG. 12C depicts another form of the concave superior surface of a float of interest. FIG. 12D is a wholly permeable float with two concave surfaces. In FIG. 12E, the bottom surface of the float composed of a permeable material is at each point thereof equidistant from a central orifice in the non-permeable material that comprises the concave superior surface and side walls of the float. FIG. 12G is a float containing a tube-like passageway for movement of liquids through the float via the passageway. The float can be configured to comprise multiple passageways. FIG. 12J is an example of a float that is configured to float at a point intermediate in the gradient and thus causes for a movement of the upper portions of the gradient around and through the permeable portions of the float into the concave portion of the float. Because the upper portions of the float comprise a permeable material, the gradient portions can flow through and over the rim of the float.

DETAILED DESCRIPTION OF THE INVENTION

Figure 1D:
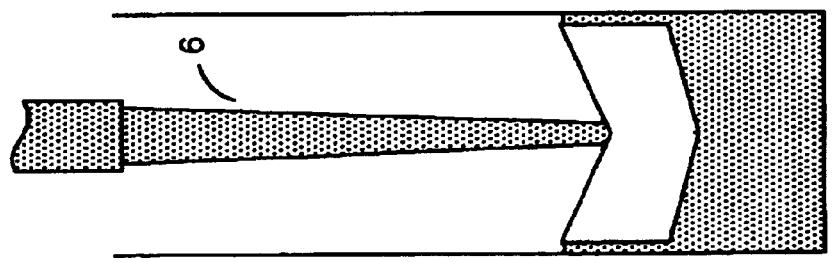
FIGS. 1A, 1B, 1C and 1D are side views showing a push-down float used for removal of one gradient layer at a time from a plurality of layers of separated materials in a vessel in accordance with one embodiment of the present invention.
Figure 1C:
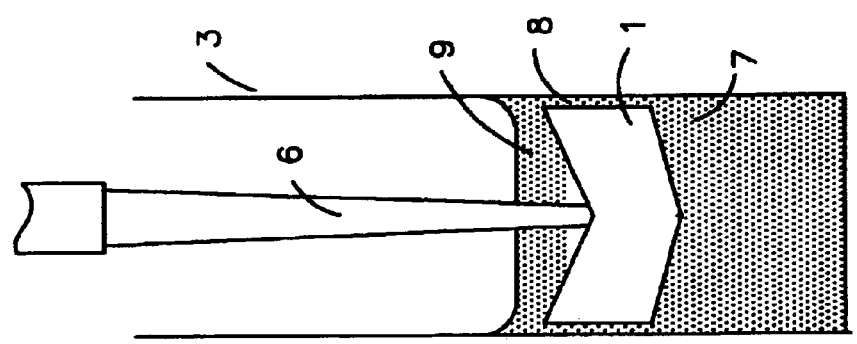
Figure 1B:
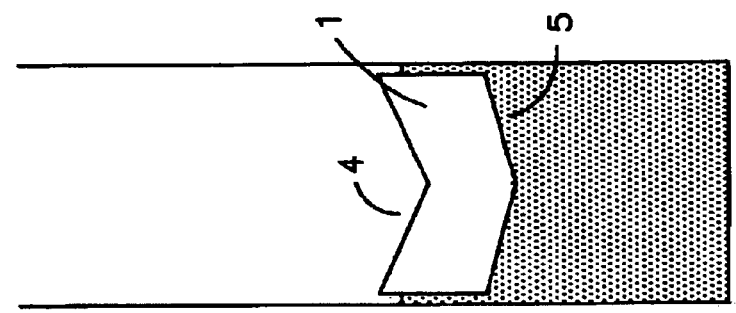
Figure 1A:
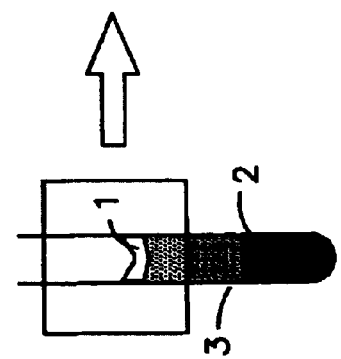

FIG. 1A shows diagrammatically a plastic float 1 floating on the top of a density gradient 2 in a vessel or tube 3. FIGS. 1B, 1C and 1D are all enlarged portions of FIG. 1A showing details of the float 1. Specifically, the top surface 4 of float 1 has a concave depression, tapering downward from the edges to the center, while the bottom 5 is convex also tapering downward from the edge to the center. The concave depression in top surface 4 of the float 1 may be conical and preferably has a central point or central portion that provides a pipette 6 (described in greater detail below) with a low point from which liquid can be suctioned, as is described in greater detail below. By inserting a pipette and engaging the superior, concave surface of the float, the float can be manipulated for reorientation or repositioning in the vessel before or following the addition of a liquid.

The upper, concave surface terminates in a rim at or near the inner surface of the containing vessel. The rim of the float of FIGS. 1A–1B is formed by the intersection of the upper concave surface with the sidewall of the float. The rim intersection of the sidewall of the float and the concave surface of the float may be of a more rounded shape then depicted in the figures when viewed from the side. A more rounded shape facilitates movement of liquid from the concave surface into the gap and thus into the area below the float when the gradient is formed. The rounded rim also facilitates movement of liquid from under the float, up through the gap and into the concavity of the upper surface when a downward pressure is applied to the float for removal of gradient portions.

The bottom 5 is preferably a conical shape but may alternatively have a spherical shape. The shape of the bottom 5 assists in directing a layer of a gradient upward toward the outer sides of the float 1 as the float is pushed downward by the pipette tip. However, the float can have a horizontal surface or a concave surface to enhance movement of liquids.

The density of the float 1 may be dictated by the choice of construction material. Thus, the float can be constructed of a single material, such as polypropylene, or of multiple materials. Also, the float can be formed of one or more materials with the materials having an increasing weight and density toward the inferior convex surface 5. Such an orientation makes the float "bottom heavy" and thus ensures the float maintains a more upright orientation in the vessel when liquids are introduced.

Alternatively the float 1 may be formed with a cavity at the convex surface 5 and preferably at the lowest part of the convex surface 5. Then a plug of a more dense material, such as a metal, is inserted into the cavity to serve as a ballast. The size of the cavity and the density of the plug can be altered to obtain a float of appropriate overall density commensurate with the liquids used and to ensure the float maintains an upright orientation in the vessel with minimal contact with the inner surface of the vessel.

The float may be made hollow or configured as a shell that is filled with a filler material of an appropriate density.

In an alternative embodiment, the float can be constructed to contain one or more channels, tubes, passageways and any such means that will enable the movement of liquids through the float. Thus, the float can be made to contain a portion of a, for example, porous material, a spongy material, a fibrous material, sintered beads, sieves and the like, that enable the movement of a gradient through the float into the concavity at the superior aspect of the float. If tubes or passageways are used, those tubes can be configured to have a valve means at the surface near the concave face of the float to enable a directional flow of fluids from the vessel into the concavity of the float. Such a valve means can include a ball valve or a flap valve.

One combination of a porous and a non-porous material into a float of interest is one where the float is comprised of a porous material and the concave surface of the float contains a non-porous material, wherein the non-porous coating does not extend all the way to the rim of the float so that on the face of the concavity is a "ring" of porous material that will allow the movement of a gradient through the float to collect in the concavity of the float for removal.

The density of the float can be configured to be of a certain and particular density so that the "float" does not necessarily float at the top of the gradient but at some intermediate level where a particular density of liquid is found following the separation process. Therefore, the actual floating position of the float of interest is at a density of liquid that is found within the gradient. Therefore, the float can be placed into the vessel of a completed gradient and allowed to attain a stable position in the gradient located somewhere intermediate with the gradient. That self-movement of the float within the gradient will cause the upper portions of the gradient to pass around and through the float into the concave surface of the float. Therefore, a portion of the upper portions of the gradient can be removed without having to manually push down the float.

In the design of the float, the intersection of the sidewall of the float and of the convex surface of the float also can be rounded to minimize sticking or wedging of the float inside the vessel and to maintain the free floating nature of the float in the vessel.

The sidewall of the float 1 that is parallel to a portion of the inner surface of the vessel is preferably long enough to prevent the float from tipping or spinning in the vessel.

The float may be made of a hydrophilic material that will minimize beading on the float. Suitable materials include wood, hydrophilic plastic, rubber, glass and so on.

The float also may be coated with a material different from that comprising the float to ensure the desired surface properties are obtained, such as minimal beading or minimal adhesion of liquids to the float.

The vessel 3 may be, for instance, a centrifuge tube having materials therein for separating cellular material or other bio-matter in a centrifuge. After the material has been separated, a plurality of layers and/or zones are created, each layer or zone having a distinct separated material or group of materials that are under study.

Removal of each layer or zone for further study or analysis is effected by the pipette 6 that uses suction to remove the desired layer or zone from the concave depression in the top surface 4. In previous manual methods for removing a single zone or layer (without the float of the present invention), a steady hand is required to position the pipette within the desired layer or zone for removal of the desired material, or the pipette must be positioned mechanically. In the present invention, the lower end of the pipette 6 is positioned above the float 1, with the lower end contacting the center of the concave top 4, as is shown in FIG. 1C. The pipette 6 is pushed downward, for instance, by hand or by a positioning device (not shown), thereby pushing the float 1 to a position beneath the upper surface of the liquid in the vessel 3.

The downward, slow and even movement of the float 1 by the pipet, forces the underlying fluid 7 to flow up through the narrow annulus 8 around the outer circumferential edges of the float 1 wherein the liquid collects in the conically shaped concave area at the top 4 of the float 1. That liquid defines a separated fluid 9, which may exceed in volume that of the concave cavity in the top of the float. As shown in FIG. 1D, the separated fluid 9 above the float is then removed by pipette 6. Pipette 6 is then moved to a separate tube in a fraction collector such as a separate tube (not shown in FIG. 1), suction is released, a small pressure is applied and the collected fraction is unloaded into the separate tube. The process is then repeated to remove further layers or zones of separated material.

It should be understood that the pipette 6 may be positioned above the float 1 by hand, by a manually operated positioning device, or may be connected to a robotic device that includes a feedback controller that includes means for determining the location of the layers in the vessel 1, and the relative position of the pipette 6 and the float 1 to provide an accurate means for removing each layer or zone of separated material.

The size of the annulus 8 is determined by the relative diameters of the inner surface of the vessel 3 and the outer surface of the float 1. Preferably, the diameters are such that the float 1 is easily moved up and down in the vessel 3 but is small enough so the float 1 can be positioned at the boundary between two separate layers or zones of material in the vessel 3. Specifically, as shown in FIG. 1C, the pipette 6 is pushed downward to a location in the vessel 1 where all of the fluid in one zone 9 is located near or above the upper edge of the float 1 and the fluid 7 beneath the float 1 is restricted to the annulus 8 and the area below the float.

Precise movement of the pipette 6 and float 1 permits isolation of the fluid 9 without disturbing the fluid 7 beneath the float 1. Once the fluid 9 is isolated from the fluid 7 above the float 1, the pipette 6 uses suction to remove the fluid 9, as shown in FIG. 1D. The isolated fluid is then deposited in a separate vessel or tube (not shown in FIG. 1.)

FIG. 2A illustrates a collecting float 10 having a slightly different shape than the float 1. Specifically, the float 10 has an axial length that is greater that its diameter. Further, the float 10 has a deep concave collecting center well 13 that has a conical shape, but a spherically shaped center bottom. The float 10 is shown in FIG. 2A floating on liquid 11 in the vessel 3. As shown in FIG. 2B, the distance that the float is pushed down determines how much fluid flows over edge 14 partially filling the center well 13 with fluid fraction 15. FIG. 2C illustrates that if the pipette tip 6 is now raised slightly, the float will rise, lowering the level of the meniscus 16 around the edge of the float, preventing further flow of liquid into the center well. As shown in FIG. 2D, the fluid 15 in the upper well may then be removed by the pipette 6. This process may then be repeated to collect consecutive additional fractions.

With slow and precise movements of the pipette 6, it is possible to move the float in such a manner as to insure slow movement of fluid from the underlying gradient up through a narrow annulus, over the defining edge of the float, and into the central well of the float from which the desired zone of the gradient is collected. The position of the float in pushed-down position defines the volume of the gradient fraction collected at each step.

The pipette 6 may be manually manipulated by a technician or scientist in order to extract a desired layer or zone of material from a tube, however, the various floats in accordance with the present invention, may be part of a robotic system, remotely controlled system, semi-automatic system or completely automated system for zone or layer removal.

Figure 3:
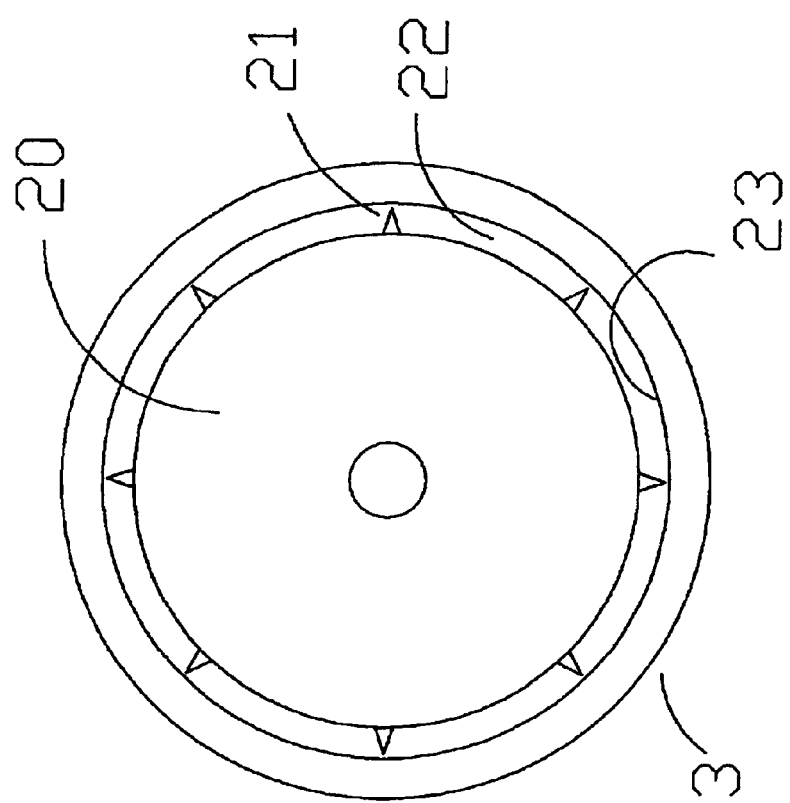
FIG. 3 is a top view of a third embodiment of a push-down float wherein the float is formed with a serrated edges to facilitate flow of fluid around the outer surface of the float.

FIG. 3 illustrates an alternative configuration in which a float 20 has vertical edge projections 21 that define an annular space 22 between the float and wall 23 of the vessel 3. This configuration allows more precise definition of the annular space between the float and the tube wall.

The floats may be made of a plastic that is less dense than water, such as polyethylene or polypropylene, and may be easily washed, or may be disposable. In manually operated systems the floats may be simply dropped onto the gradient, and their diameter and length are such as to prevent inversion. The upper portion of the float may be a hydrophobic material to facilitate removal of the gradient from the concave depression. Alternatively, the concave surface can be coated with a hydrophobic material.

Figure 4A:
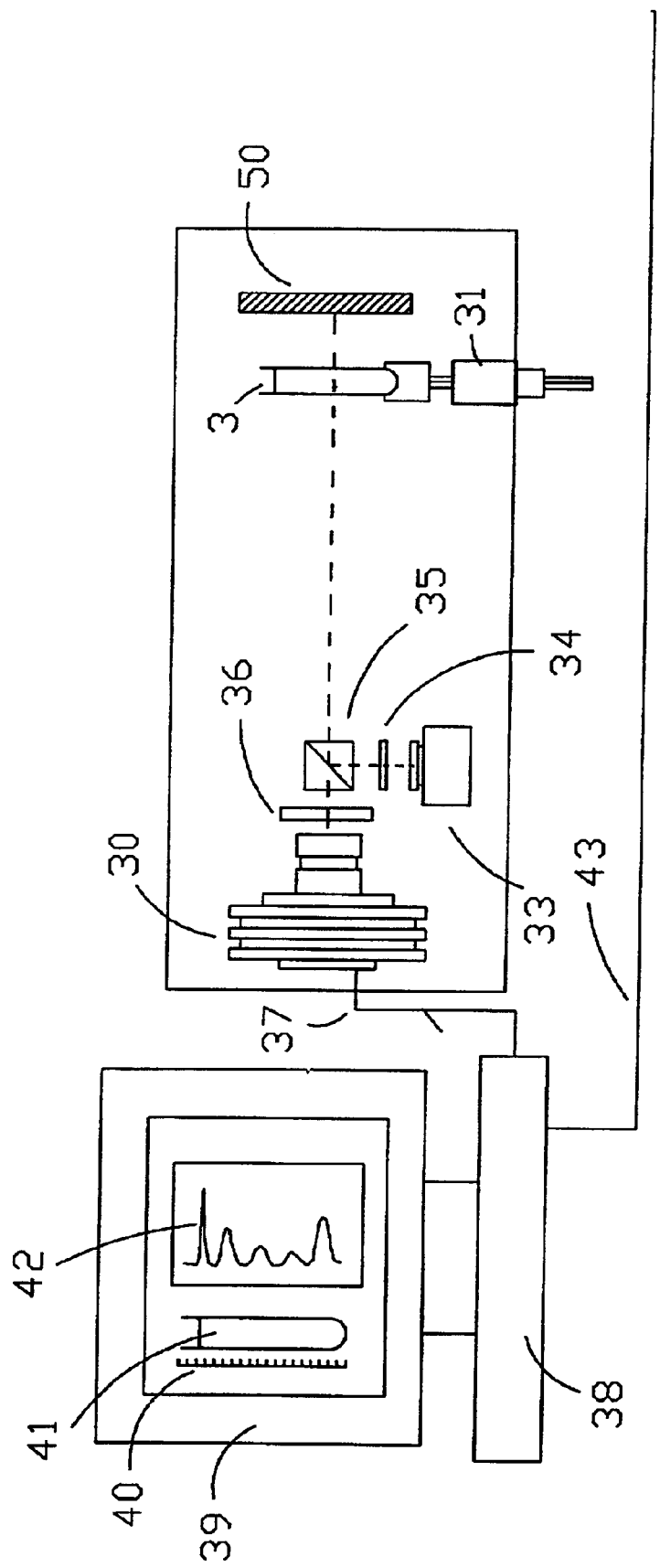
FIGS. 4A and 4B are a side schematic view of an automatic pipetting system including an electronic scanner for determine a location of particle zones in a gradient and controlling recovery of the particle zones in the gradient.
Figure 4B:
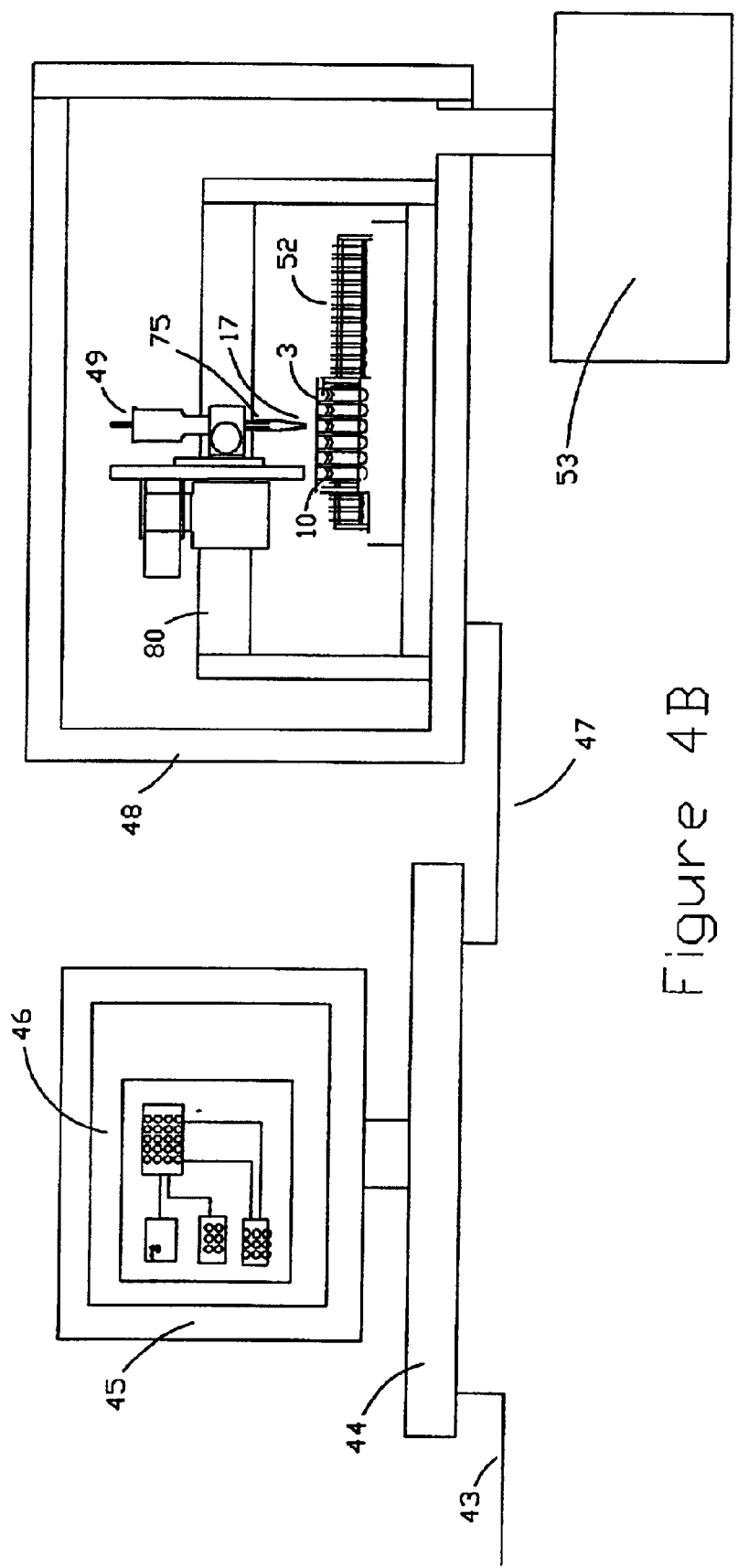

FIGS. 4A and 4B illustrate diagrammatically one embodiment of an automated system for scanning and unloading gradient tubes where portions of a gradient in the tubes are removed. Unloading of portions of the gradient in a tube may be facilitated by scanning optically identifiable differences between layers, zones or regions of the gradient in order to determine the size or depth of each region of the gradient. Under conditions where the fluids that make up the gradient have no visible differences within normal lighting conditions, epifluorescent or back illumination may be used to detect fluorescence. It should be understood that dyes or other visible markers may also be used in order to provide visible delineations between layers or zones of the gradient.

As shown in FIGS. 4A and 4B, a digital camera 30 is focused on one vessel 3 (a centrifugal tube) for acquiring images of density gradients in the vessel 3. A computer 38 is connected to the camera 30 for controlling the camera and further for analyzing and displaying the images acquired by the camera 30 of the vessel 3. A second computer 44, shown in FIG. 4B, is connected to the first computer 38 via a communication line 43 such that information from the first computer 38 may be transmitted to the second computer 44. The second computer 44 is connected to a robotic X-Y device 80 via line 47. The X-Y device includes a gripper 75 that selectively grips a sample recovery pipette 17 and includes software for controlling movement of the pipetter 49 on the X-Y device 80. The gripper 75 includes a track (not shown) that allows the gripper 75 to be vertically moved to position the pipetter 49 selectively in and out of vessels 3. The second computer 44 includes software, further described below, for controlling the vertical position of the gripper 75 thereby accurately positioning the pipetter 49, tip 17 and float 10 (as shown in FIG. 2C) at a level within the vessel 3 for sample recovery. The second computer 44, shown in FIG. 4B, also includes software for controlling suction provided to the pipetter 49 for removing a recovered zone or layer of a gradient captured from the well of the float 10. The suction source (not shown) is connected to the pipetter 49 to selectively provide suction and the computer 44 is electronically connected to the suction source for controlling application of suction to the pipetter 49 for sucking up a desired layer or zone, and releasing or expelling the isolated layer or zone into a separate tube, as is described in greater detail below.

In the depicted embodiment in FIGS. 4A and 4B, the digital camera 30 is focused on one of the vessels 3 carrying the density gradient. A light source 33 provides exciting light through filter 34 and is reflected off split beam prism 35 to illuminate the vessel 3. An emission filter 36 filters out the exciting wavelengths and stray light, and isolates the wavelengths from the fluorescent dyes used or from natural color or fluorescence of bands in the density gradient in the vessel 3. Signals from camera 30 are transmitted through cable 37 to microcomputer 38 and the results are displayed on CRT 39. The image on the CRT 39 may include, for instance, an image of a scale 40 indicating heights at the focal plane of camera 30 (and corresponding to the heights of the various layers of the density gradient in the vessel 3), a black and white, pseudocolor, or color translation image 41 of the vessel 3, and plot of light intensity vs. distance 42 along the height of the vessel 3. The computer 38 is further provided with software for determining the height of each zone or layer of the density gradient from the graph plot of light intensity vs. distance 42. Vertical movement of the pipetter 49 is determined from the height of each zone or layer such that each layer may be removed one at a time from the vessel 3 and moved to a smaller tube 52.

In FIG. 4B, the X-Y device 80 and the pipetter 49 are located within a sealed compartment 48 that is provided with temperature controlled via a cooling unit 53. The cooling action of the cooling unit 53 keeps the density gradients in the plurality of vessels 3 at a temperature where diffusion of the various layers of the gradient is retarded. Within the compartment 49 there is a plurality of vessels 3, each having a density gradient formed as a result of, for instance, centrifuging. A group of smaller tubes 52 are disposed adjacent to the vessels 3, each tube 52 for receiving recovered zones or layers from the density gradient taken by the pipetter 49 from the vessels 3. Each tube 52 is provided for receiving one gradient layer or zone from a single vessel 3.

It should be understood that there are many possible configurations for location of the camera 30. In one configuration (shown in FIG. 4A), the camera is focused on a vessel 3 that has been moved from the compartment 48 for scanning by the camera 30. The vessel 3 is later returned to the compartment 48 for layer removal. Further, the vessel 3 may be one of a plurality of almost identical vessels each having approximately the same density gradients. Therefore, scanning of one vessel 3 of the plurality provides height and depth information for all of the plurality of vessels 3 in the compartment 48. However, the system shown in FIGS. 4A and 4B may be used in a manner such that each and every vessel 3 is scanned individually for determination of height of each zone or layer of density gradient.

In an alternative configuration (not shown), the camera 30 may be focused on the vessels 3 within the compartment 48. In other words, the camera 30 may be used in real time for determining the depth, or overall height of each zone or layer within the temperature controlled compartment 48 without removal of the vessels 3 from the compartment 48.

It should also be understood that the computers 38 and 44 may be two separate computers or may alternatively be a single computer having a plurality of software functions enabling the single computer to scan a vessel 3 to determine zone thickness and depth. The computer means also will control movement and sample recovering functions of the pipetter 49.

Figure 5:
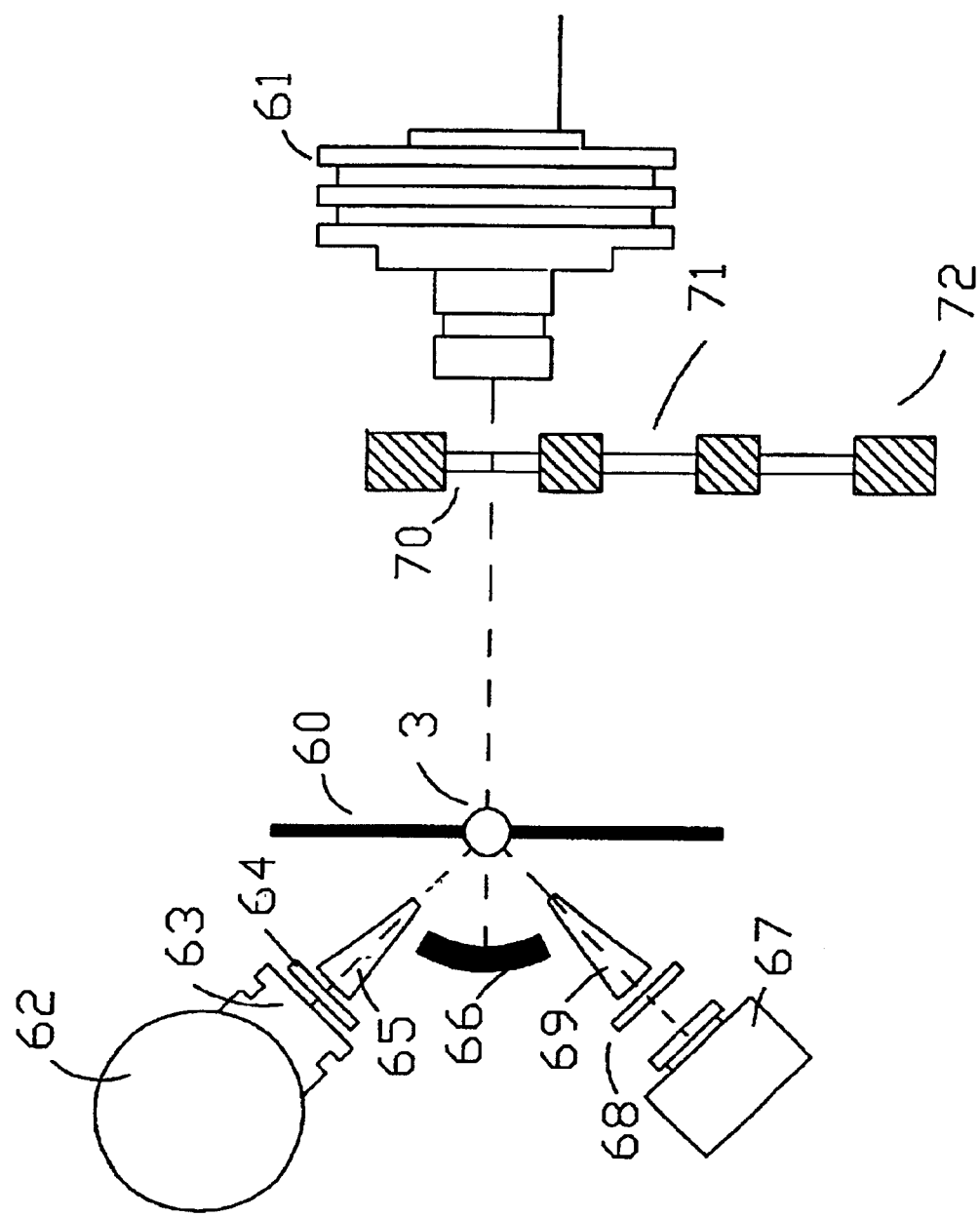
FIG. 5 is a side view of an alternate embodiment of an electron scanner used in the automatic pipetting system depicted in FIG. 4, on an enlarged scale, showing details of the alternate embodiment of the electronic scanner.

FIG. 5 is a top view, looking down, that illustrates diagrammatically another configuration of a digital camera 61 having two light sources 62 and 67, and movable emission filters 70–72 used to produce color translation images.

Color translation may be used to make readily visible differences between images obtained in the ultraviolet, a combination of ultraviolet and visible, or closely spaced intervals in the visible. Thus, for example, images obtained at 450, 415 and 380 nm may be rendered as red, green and blue, as may images obtained in the visible at 530, 520 and 510 nm. The wavelengths chosen for translation depend on the dyes used, or the native fluorescence of the particles to be separated.

In FIG. 5 clear, transparent tube 3 is held vertical to the page by curved edge shielding supports 60, and is illuminated by solid square light pipe 65 transmitting light from the light source 62 through collimating lens 63 and excitation filter 64 to illuminate the entire length of tube 3. To accommodate a wider range of incident or exciting wavelengths a second light source, 67 is provided together with filter 68 and solid light pipe 69. A curved black panel 66 is provided behind the centrifuge tube 3 to reduce the stray light reaching the digital camera. A series of movable filters 70, 71 and 72 may be moved in front of the camera 61 to isolate emitted fluorescent light from exciting wavelengths to enhance image processing by color translation.

Figure 6:
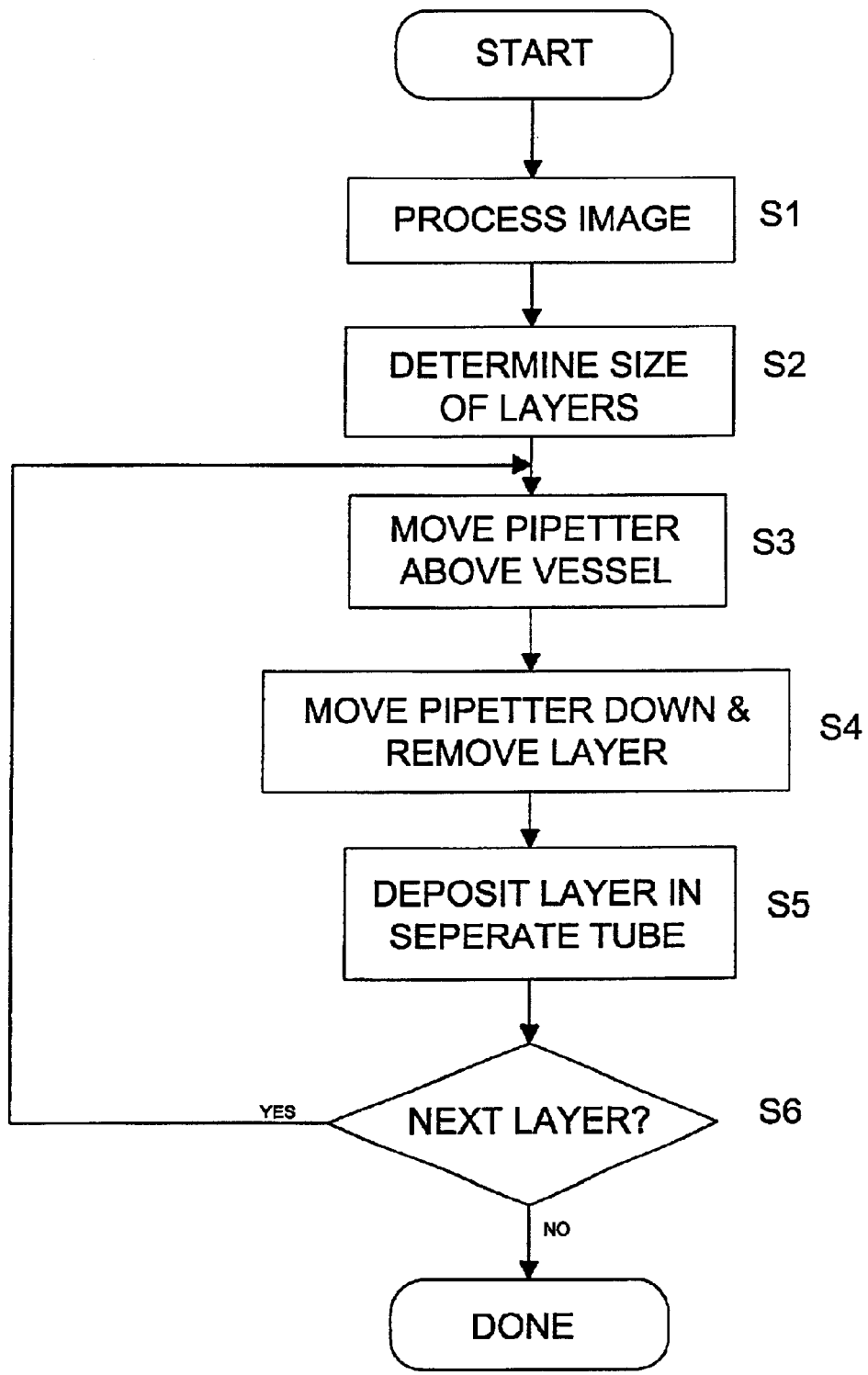
FIG. 6 is a flowchart showing operational control steps for the automatic pipetting system depicted in FIGS. 4A and 4B.

FIG. 6 is a flowchart showing operational steps for the system depicted in FIGS. 4A and 4B. In step S1, the computer 38 obtains an image of the vessel 3 from the camera 30. In step S2, the computer 38 uses the image data obtained from the camera 30 to determine the depth that the float 10 must be moved to in order to recover each individual zone or layer of the density gradient in the vessel 3. For instance, from the image 41 and graph 42, the computer 38 determines that there are five (5) distinct optically recognizable zones, each zone corresponding to a peak on the graph 42 and four intermediary boundary layers, one boundary layer located between each pair of adjacent peaks. Depending upon user input or preprogrammed instructions, the computer determines the number of separate movements necessary for removing each zone and/or boundary layer of the density gradient in the vessel 3. For example, previous user input may designate that boundary layers between each of the five zones are to be separated from the five zones. Therefore, nine separate operations are necessary to extract the five layers and the four boundary regions from the vessel 3 and move each zone and boundary layer to a separate individual tube 52.

In another example, previous user instruction may designate that the five zones are to be taken with a portion of the boundary layer divided equally between zones. In other words, each boundary layer is divided between adjacent zones. Therefore, the depth and thickness of each zone would include one entire peak of the graph 42 plus half of the boundary layer between zones.

In yet another embodiment of the present invention shown in FIG. 4B, the computer 44 is provided with predetermined heights and thickness of each zone or layer of the density gradient in the tubes 3. The predetermined heights and thickness of each zone or layer may be entered in manually by an operator or stored from a previous scan of one of the plurality of vessels 3. In a series of sample separations or tests, where reproducible density gradients are produced in large numbers, scans of the heights and thickness of zones or layers of the gradient may not be necessary. Rather, only predetermined dimensions are needed to recover the layers and move each layer from a vessel 3 to separate tubes 52. Thus computer 44 and the complete pipetting device including the compartment 48, the X-Y device 80, pipetter 49, gripper 75, vessels 3 and tubes 52, all described above with respect to FIG. 4B may be used as a stand alone device.

At step S3 in FIG. 6, the pipetter 49 is moved by control commands sent to the X-Y device 80 from the computer 38 or 44 (depending upon whether one or two computers are employed) to an (x,y) location above one of the vessels 3. At step S4, the pipetter 49 is moved downward to the determined depth for the zone or boundary layer being recovered thereby pushing the float 10 in the vessel 3 downward. Downward movement of the float 10 causes the desired portion of the density gradient to spill into the well 13, as shown in FIG. 2. After a predetermined time period (for instance, a couple of seconds) the computer may optionally move the pipetter upward a small amount to stop flow of fluid into the well 13. Next the computer engages suction or vacuum from a vacuum source (not shown) to the pipetter 49 causing the zone or layer in the well 13 to be drawn into the pipetter 49. At step S5 the computer causes the pipetter 49 to be moved to an (x,y) location above one of the tubes 52 and the fluid in the pipetter 49 is thereafter deposited in the tube 52 for later processing or analysis. In step S6, the computer determines whether or not there are more layers or zones to be recovered. If there are more layers or zones to be recovered, the process returns to step S3 for removal of the next layer or zone. If all layers or zones have been recovered, the operation is completed. The complete operation is repeated for each vessel 3 having a density gradient to be recovered.

Figure 7:
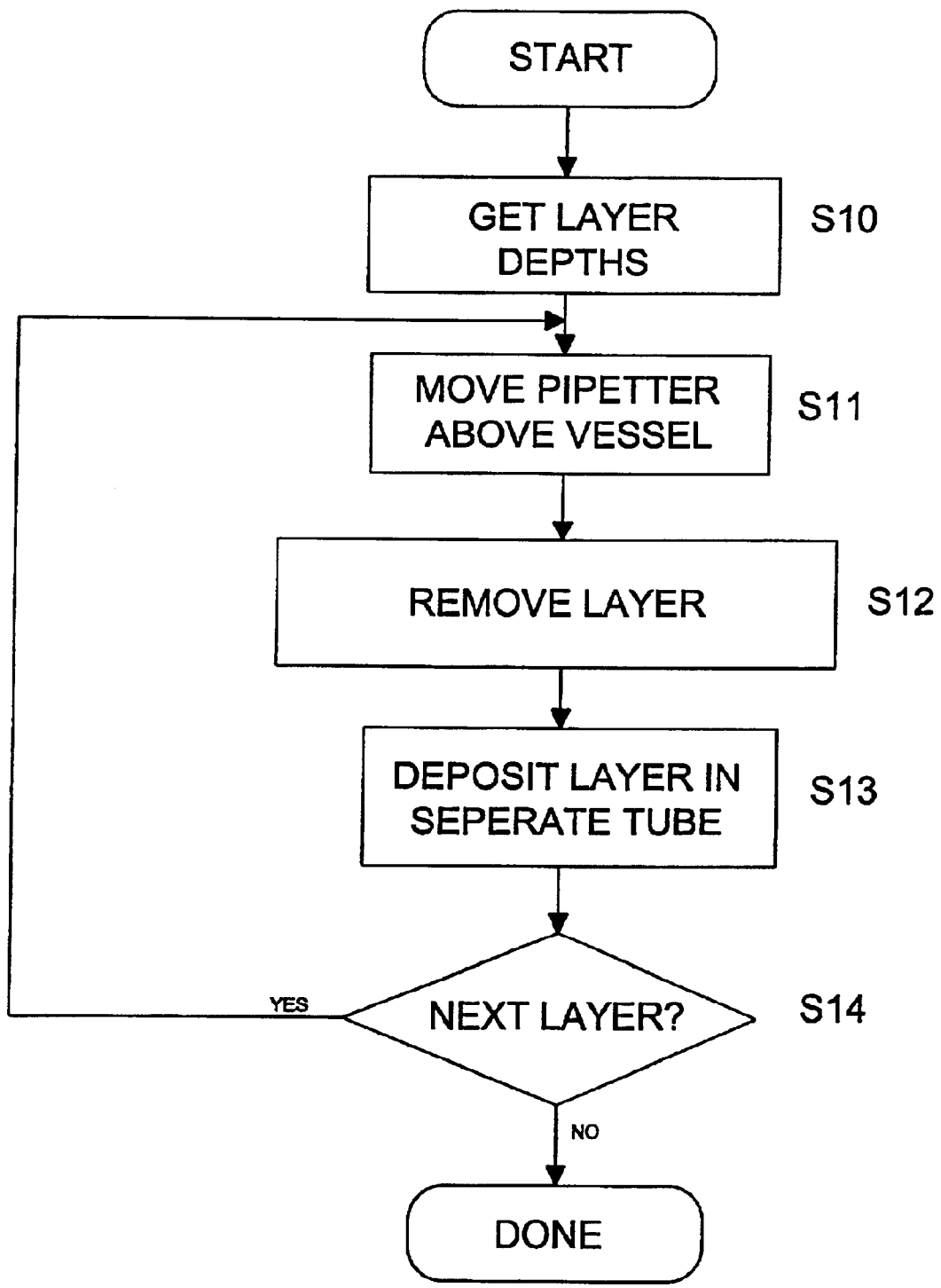
FIG. 7 is a flowchart showing operational control steps for the automatic pipetting system depicted in FIG. 6.

FIG. 7 is a flowchart showing operational steps for a stand-lone system based on the system depicted in FIG. 4B. In such a system, the height of the various layers and zones in the density gradient may be previously determined, rather than being optically determined in situ. In step S10, the computer 44 obtains information concerning height and size of each individual zone or layer of the density gradient in the vessel 3. For instance, the height and size of each zone or layer may be manually inputted into the computer or may be stored in long term memory (such as a hard drive) for later retrieval. At step S11 in FIG. 7, the pipetter 49 is moved by computer 44 to an (x,y) location above one of the vessels 3. At step S12, the pipetter 49 is moved downward to the determined depth for the zone or boundary layer being recovered thereby pushing the float 10 in the vessel 3 downward. Downward movement of the float 10 causes the desired portion of the density gradient to spill into the well 13. After a predetermined time period (for instance, a couple of seconds) the computer may optionally move the pipetter upward a small amount to stop flow of fluid into the well 13. Next the computer engages suction or vacuum from a vacuum source (not shown) to the pipetter 49 causing the zone or layer in the well 13 to be drawn into the pipetter 49. At step S13 the computer causes the pipetter 49 to be moved to an (x,y) location above one of the tubes 52 and the fluid in the pipetter 49 is thereafter deposited in the tube 52 for later processing or analysis. In step S14, the computer determines whether or not there are more layers or zones to be recovered. If there are more layers or zones to be recovered, the process returns to step S11 for removal of the next layer or zone. If all layers or zones have been recovered, the operation is completed. The operation is repeated for each vessel 3 having a density gradient to be recovered.

Figure 8:
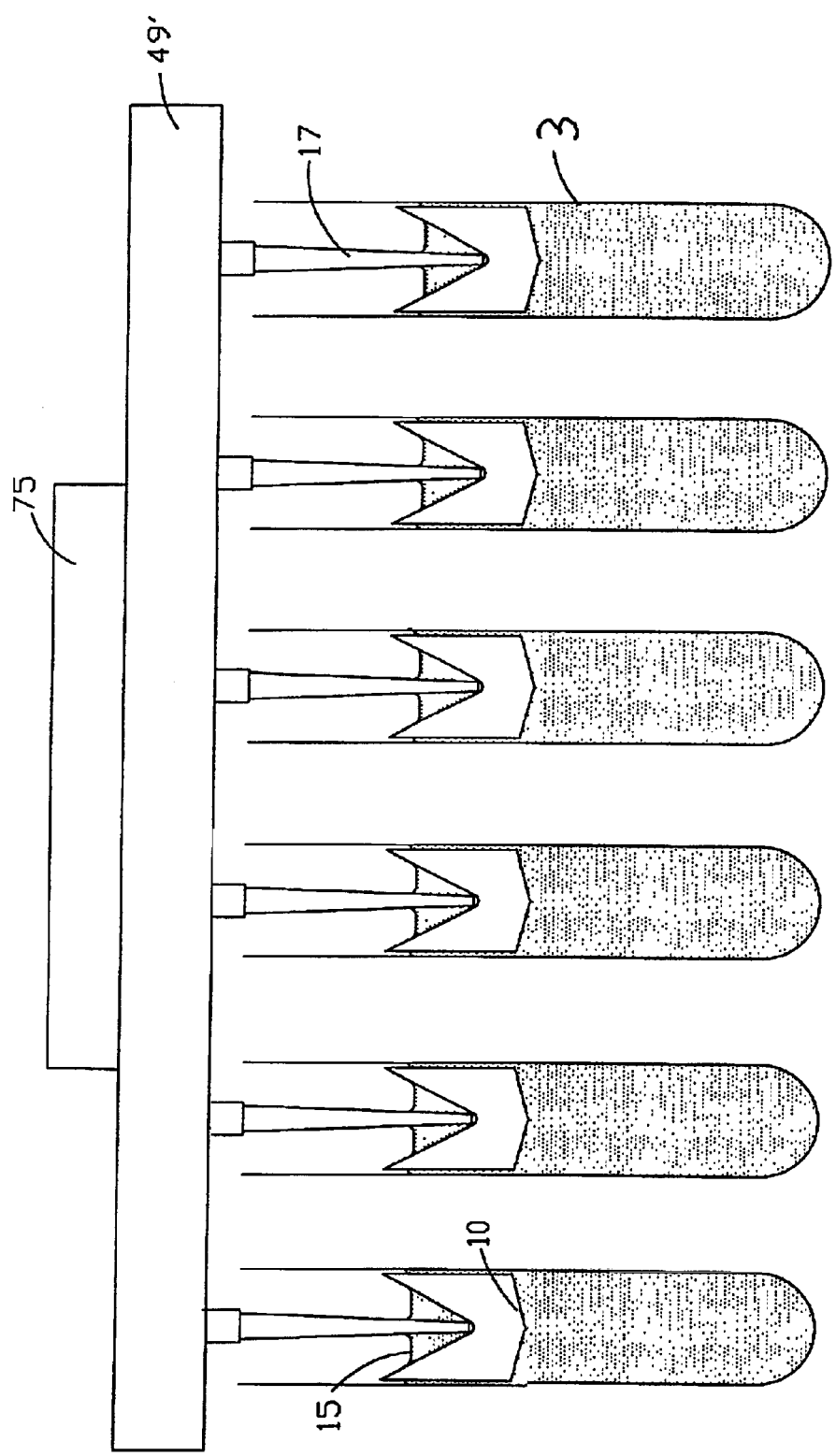
FIG. 8 illustrates multiple-parallel unloading of gradients.

It should be understood that although only one pipetter 49 is shown in FIGS. 4B and 6, a pipetter 49' shown in FIG. 8 has a plurality of pipetter tips 17 that may be employed for simultaneous removal of zones or layers 15 from multiple vessels 3, each vessel 3 having a corresponding float 10 therein. For instance, similar layers 15 of density gradients in a series of six (6) vessels 3 each having the float 10 on the upper surface of the density gradient may be manipulated all at the same time if the density gradients in each vessel 3 are similar. In such an arrangement, the pipetter 49' having multiple tips supported by gripper 75 (and suction means not shown) may be arranged to remove identical fractions simultaneously from each vessel of a set of vessels, each vessel having identical gradients. Each zone or layer (now a fraction of the gradient) is thereafter transferred to a corresponding set of collecting tubes 52.

Figure 9A:
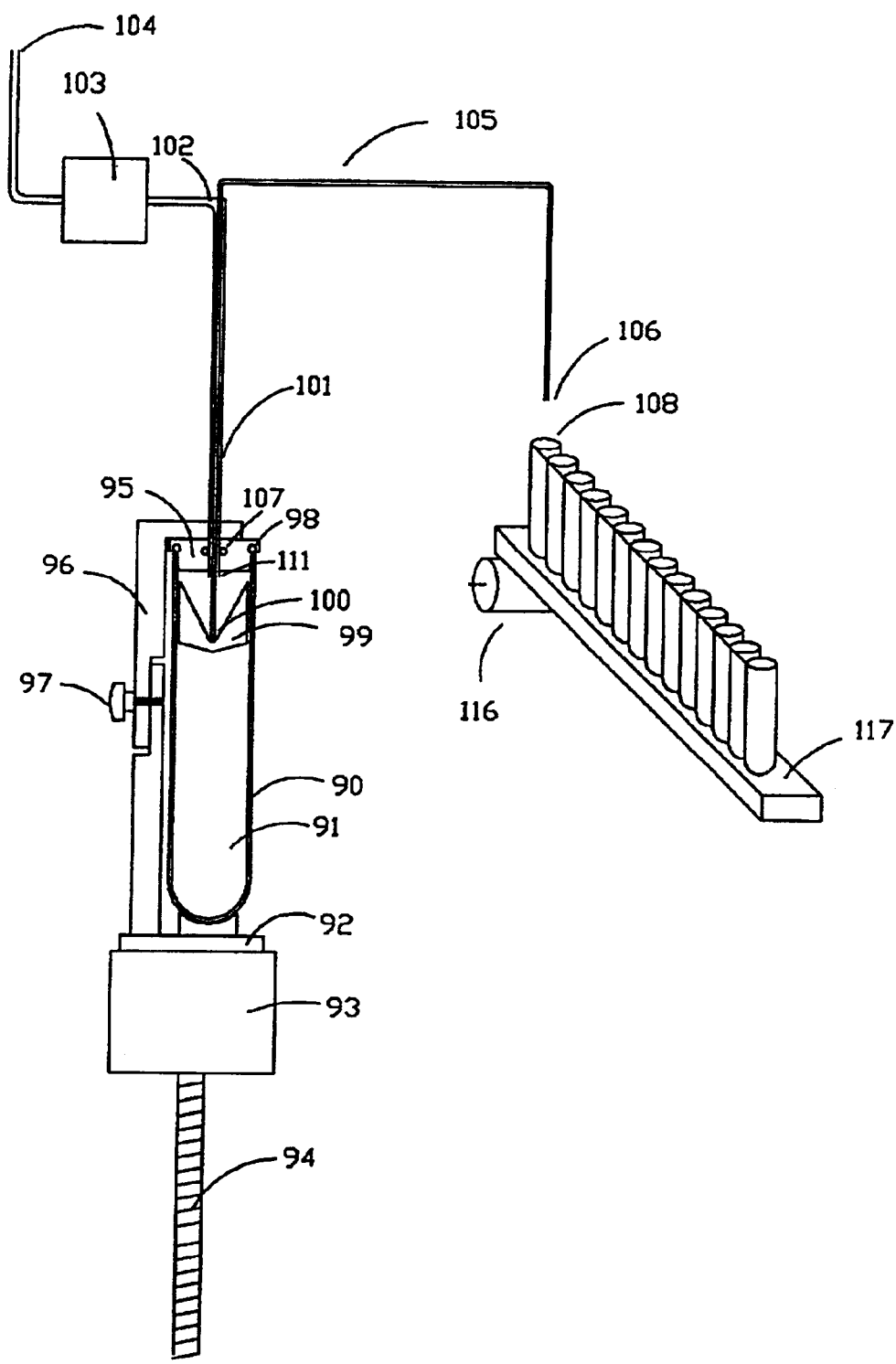
FIGS. 9A through 9D show an alternative collection system in which the collected fractions are recovered by air pressure either singly or in parallel with the float remaining in a generally constant position, while the vessel is moved upward in stages.

An alternate embodiment of the float design is illustrated in FIGS. 9A through 9D in which the sample layers are recovered using air pressure instead of a partial vacuum. In this design, as shown in FIG. 9A, centrifuge tube 90 containing density gradient 91 containing separated particle zones (not shown) is supported on holder 92 which is driven upward by stepping motor 93 using screw 94. The top of the centrifuge tube 90 is closed by cap 95 which is held tightly in place by clamp 96 and adjustment screw 97 and the top sealed by o ring 98. Float 99 is positioned on the gradient and tube 90 is move up until the tip of recovery tube 100 touches the bottom of the depression in the float. The concentric tubes 101 include outer tube 102 which serves to conduct air under pressure to the chamber above the float when valve 103 is opened to air under pressure in tube 104. The innermost of the concentric tubes is the transfer tube that has tip 100 touching the bottom of the float, and tip 106 positioned over the first collecting tube 108. Concentric tubes 101 are lightly sealed as they pass through cap 95 by O ring 107. Thus, as tube 90 and associated components are driven upward against stationary tip 100, float 99 is slowly pushed down, defining the first volume element of the gradient to be collected. After each volume element is defined, and the upward movement of the tube 90 stops, air pressure is introduced through valve 103 expelling the fluid above the float into one of the collecting tubes in the series of tubes supported by tube holder 117 which is driven horizontally by stepping motor 116 between zone collections. Note that the end of the air displacement tube 111 is always above the level of fluid around tube 99.

Figure 9B:
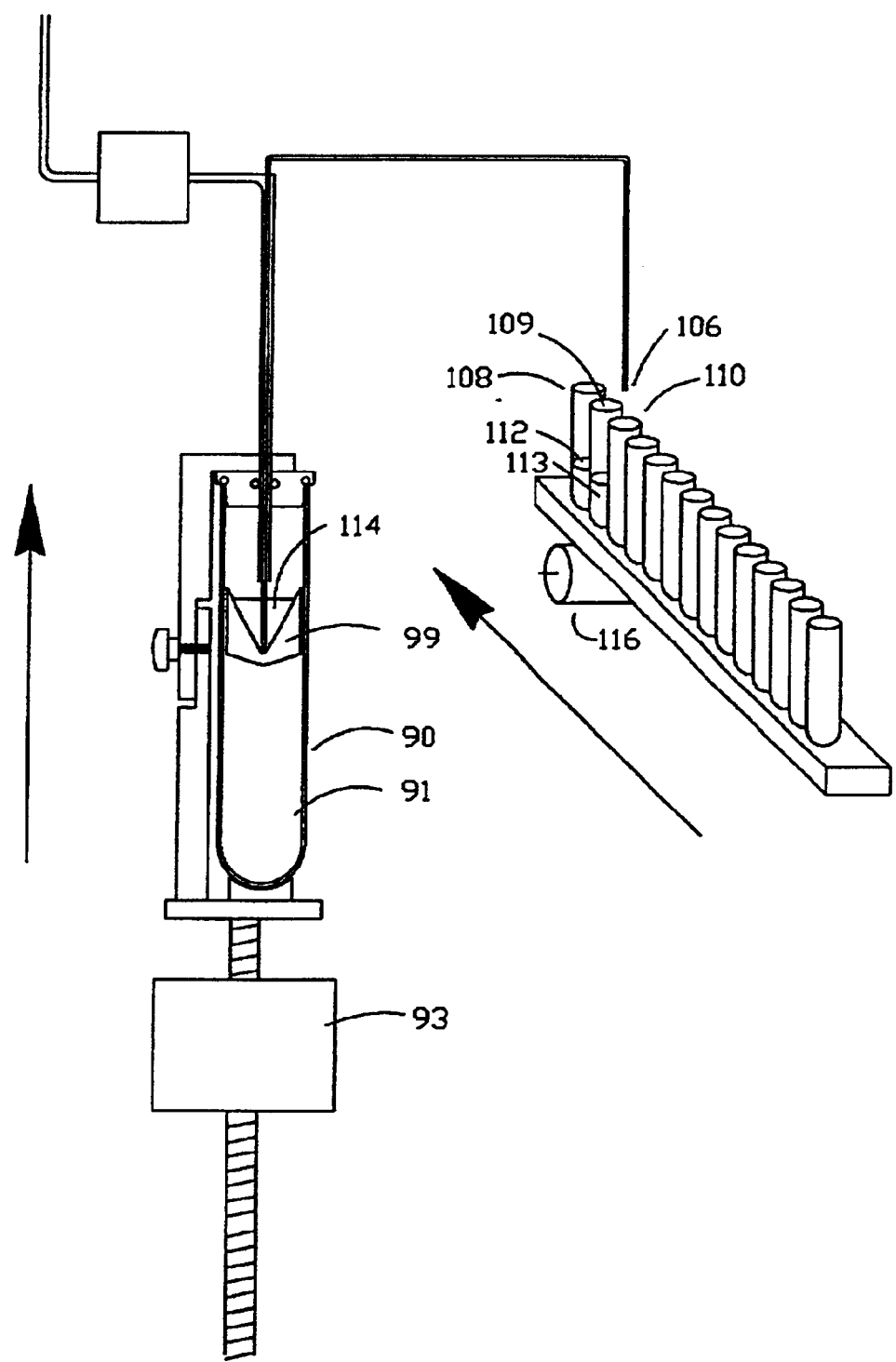
Figure 9C:
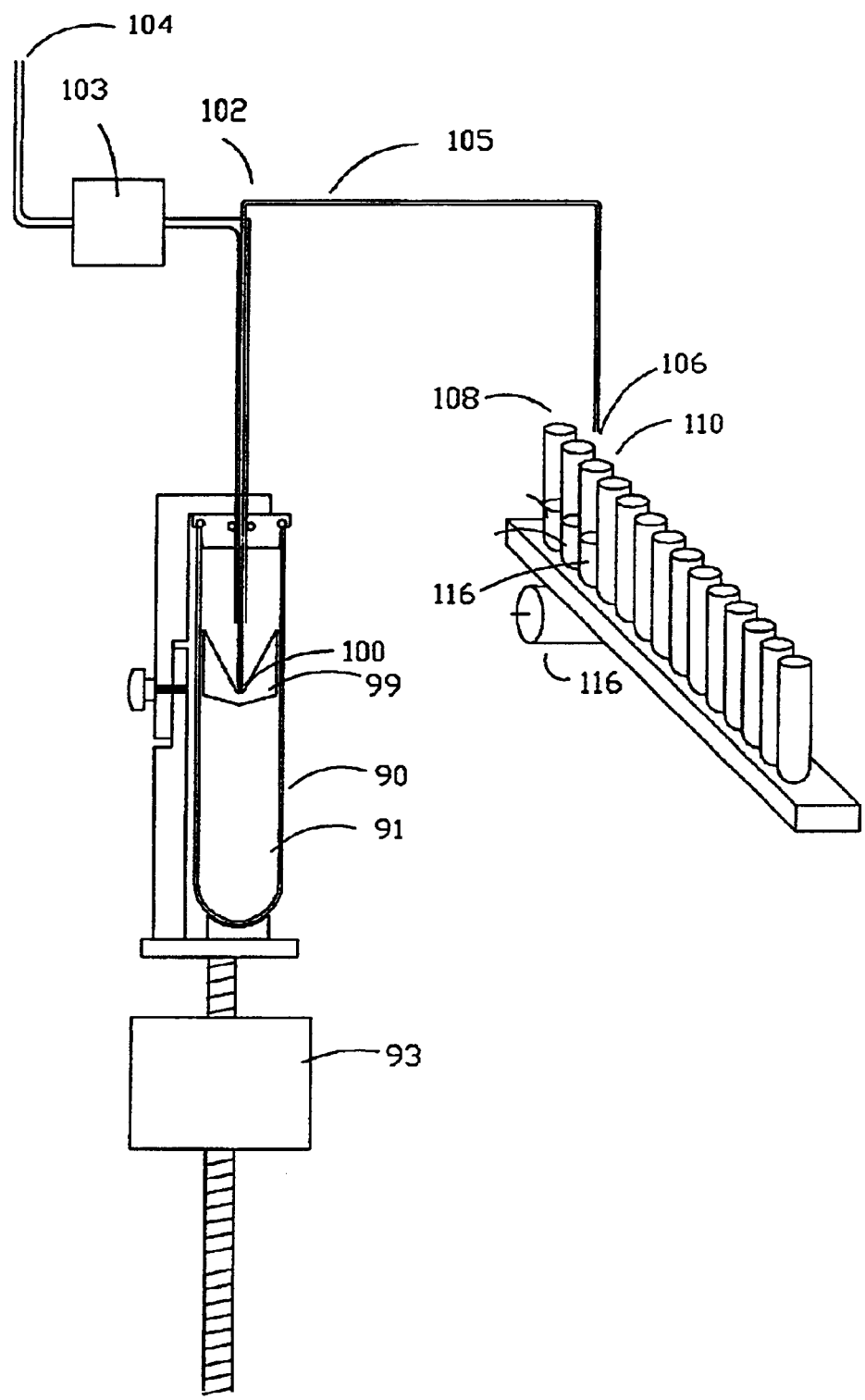
Figure 9D:
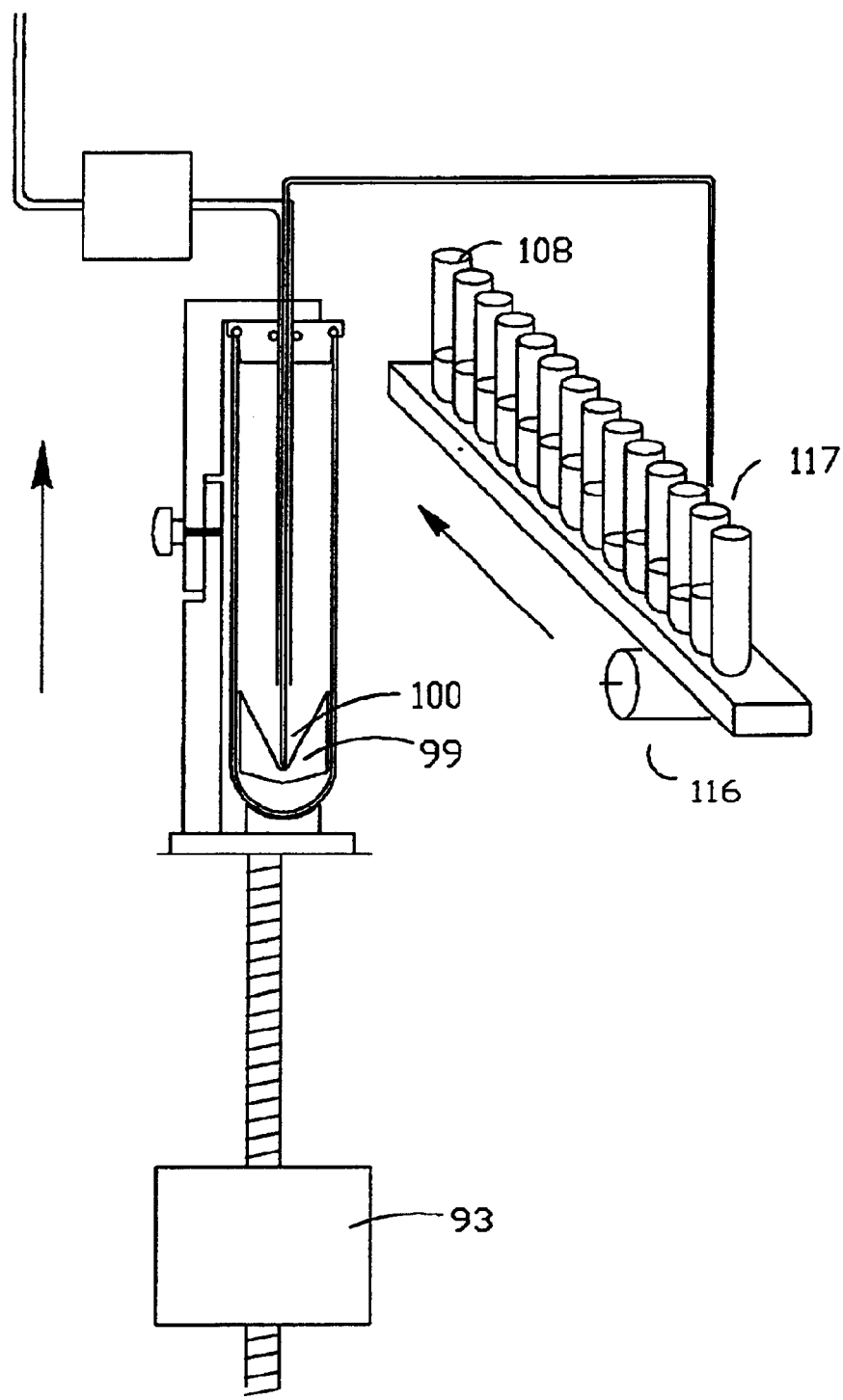

The collecting process is illustrated in FIG. 9B in which fluid zone 114 is collected in float 99 as tube 90 is pushed up by motor 93. Two previously collected sample zones 112 and 113 are shown in their respective tubes 108 and 109. Motor 111 has moved the set of collecting tubes to position tip 106 over tube 115. As shown in FIG. 9C, air pressure through valve 103 expels the fluid above the float through transfer tube tip 100, out tip 106, and into tube 115, as fraction 116. FIG. 9D illustrates the completion of the collection process in which motor 93 has driven float 99 against the bottom of the centrifuge tube, and the collection tubes 107 to 117 contain the collected fractions. This process is effected by the coordinate movements produced by motors 93 and 116.

For full automation of the gradient collection process it is important to have means for both introducing the collection floats at the start of collection, and for recovering them after collection is complete. A modified push-down float 120 adapted to this purpose, shown in FIG. 10A, has an annular groove 121 inscribed on an inner surface of upper cavity 122 defining a corresponding inwardly protruding ridge which allows a grasping tool 125 shown in FIG. 10B to grasp and move the float for insertion and removal.

FIGS. 10B, 10C and 10D illustrate how push-down gradient-collection floats may be robotically loaded into centrifuge tubes containing gradients and separated particles after centrifugation. A stack of modified collection floats 123 is contained initially in cylinder 124. These are removed one by one by gripper 126 that includes two identical spring members 126 that are spring biased to move away from one another. The spring members 126 are closed by movement of rollers 127 that are positioned vertically by support 128 driven by mechanism 129, which in turn is moved vertically by a mechanism not shown. In the configuration of FIG. 10B, the gripper, rollers 127, support 128 and mechanism 129 are adjusted to move the gripper surfaces 125 close together and below the level of the ridge so that the gripper surfaces 125 may be inserted into the groove 121.

In FIG. 10C, rollers 127 have been moved upwardly in reference to gripper 126, causing the gripper surfaces 125 to move outwardly to engage groove 121. This in turn allows the entire gripper apparatus and the top float to be raised and, as shown in FIG. 10D, to be inserted into tube 3 on top of gradient 130. When the gradient has been recovered, the loading procedure can be reversed, as shown in FIGS. 10E and 10F, to recover the float.

Figure 11:
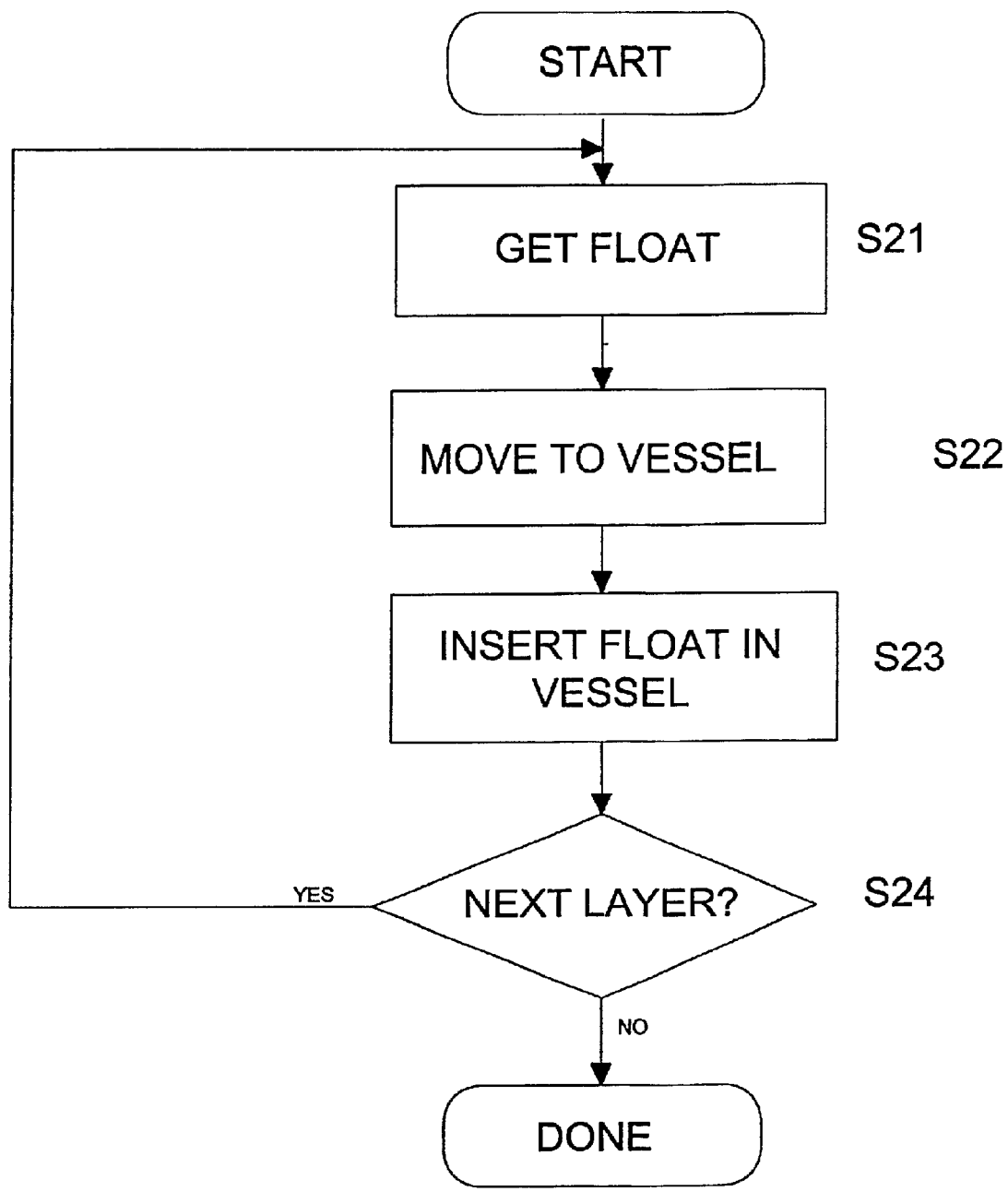
FIG. 11 is a flow chart of the steps involved in positioning the floats in gradient tubes.
Figure 12A:
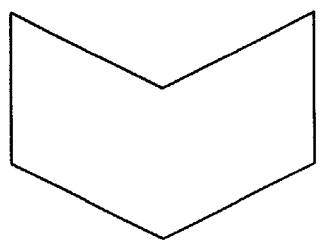
FIGS. 12A–12J depict alternative forms of a float. In the figures, the solid black regions depict materials impervious to a gradient liquid. The gray regions depict materials that enable liquids to flow therethrough.
Figure 12B:
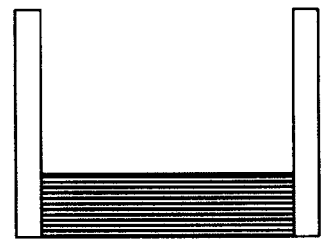
Figure 12C:
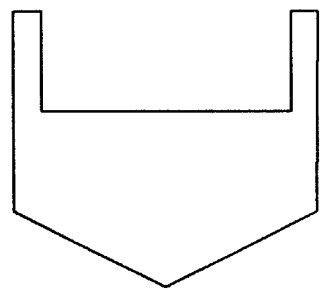
Figure 12D:
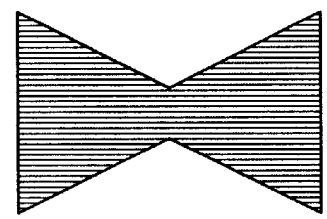
Figure 12E:
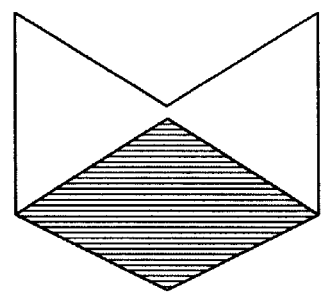
Figure 12F:
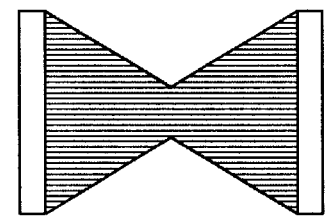
Figure 12G:
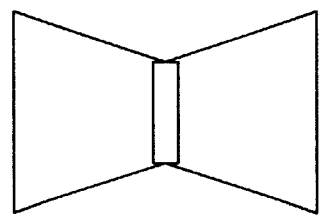
Figure 12H:
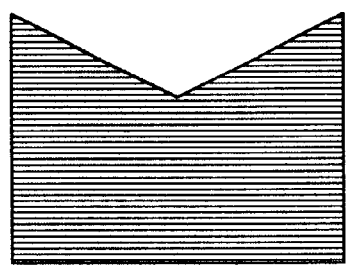
Figure 12I:
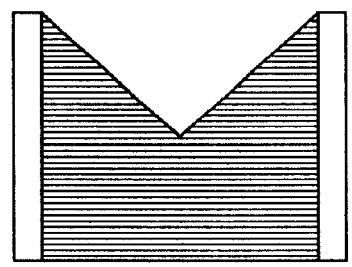
Figure 12J:
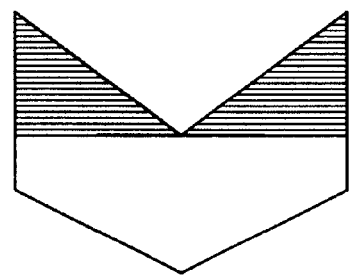

The complete process is shown diagramatically in the flowchart of FIG. 11 in which the gripper grips a float at step S21, moves to a vessel in step S22, inserts the float 10 into a vessel at step S23, then determines whether or not more floats are to be inserted in step S24. If more floats 10 are to be inserted in more vessels, the process returns to step S21. Otherwise, the operation is completed and processing can move to removal of layers as described above with respect to either FIG. 6 or FIG. 7.

It should be understood that the combination of methods for unloading sets of precision gradients may utilize optical data from the gradients themselves or may include preprogramming such that gradient layers are withdrawn based upon predetermined dimensions. Cell and tissue extracts autolyze and degrade with time. If gradients are collected in small increments, then analyzed to locate subcellular organelles among these fractions, and the data then used to identify which fractions should be combined for high resolution proteomic analysis, considerable time will have elapsed, and the samples will have been degraded. The solution to this problem in the present invention is the direct combination of means for optically analyzing gradients combined with mechanical means for directly recovering the volume elements containing specific organelles.

For example, mitochondria possess iron-containing enzymes lacking in the endoplasmic reticulum fraction, giving mitochondria in bulk a distinct reddish brown color. In contrast, the endoplasmic reticulum is white with a trace of yellow. Hence these two fractions can be distinguished by eye. This difference has not previously been used to monitor the separation of these two fractions.

A wide variety of dyes have been described as specific to a subcellular organelle, but few of them have been used to identify organelles in homogenates, and none have previously been used to identify organelles in liquid density gradients in order to locate them for recovery.

While the invention has been described in connection with the specific embodiments thereof, it will be understood that the invention is capable of further modifications. The claims are intended to cover variations, uses and/or adaptations of the invention following, in general, the principles of the invention and including such departures from the present invention from the present disclosure, within known and customary practice within the art to which the invention pertains.

This application is a continuation-in-part of U.S. Ser. No. 09/628,340 filed Jul. 28, 2000, the contents of which herein are incorporated by reference in entirety.

REFERENCES

Anderson, N. G., ed. The Development of Zonal Centrifuges. National Cancer Institute Monograph 21, 1966

Price, C. A. Centrifugation in Density Gradients. Academic Press, N.Y. 1982

Scheeler, P. Centrifugation in Biology and Medical Science. John Wiley & Sons N.Y. 1981

Anderson, N. G. A simple method for observing refractive index gradients in liquids. Biochim Biophys Acta 25: 418, 1957

Anderson, N. G., Bond, H. E., and Canning, R. E. Analytical techniques for cell fractions. I. Simplified gradient elution programming. Analyt Biochem 3: 472–478, 1962.

Anderson, N. G., and Rutenberg, E. Analytical techniques for cell fractions. A simple gradient-forming apparatus. Anal Biochem 21: 259–265, 1967.

Candler, E. L., Nunley, C. E., and Anderson, N. G. Analytical techniques for cell fractions. VI. Multiple gradient-distributing rotor (B-XXI). Anal Biochem 21: 253–258, 1967

Albright, J. F., and Anderson, N. G. A method for the rapid fractionation of particulate systems by gradient differential centrifugation. Exptl Cell Research 15: 271–281, 1958

Anderson, N. G., Bond, H. E., and Canning, R. E. Analytical techniques for cell fractions. I. Simplified gradient elution programming. Analyt Biochem 3: 472–478, 1962.

Fisher, W. D., G. B. Cline, and Anderson, N. G. Density gradient centrifugation in angle-head rotors. The Physiologist 6: 179, 1963.

Anderson, N. G., and Rutenberg, E. Analytical techniques for cell fractions. A simple gradient-forming apparatus. Anal Biochem 21: 259–265, 1967.

Candler, E. L., Nunley, C. E., and Anderson, N. G. Analytical techniques for cell fractions. VI. Multiple gradient-distributing rotor (B-XXI). Anal Biochem 21: 253–258, 1967

Luthe D S A simple technique for the preparation and storage of sucrose gradients. Anal Biochem 135:230–2, 1983

Hirst W, Cox R A A method for predicting the location of particles sedimenting in sucrose gradients. Anal Biochem 131:51–68, 1983

Clark A G, Gellen J W Hydrostatically balanced gradient-formers: programming of gradients. Anal Biochem 103:94–100, 1980

Olenick J G, Lorenz P E A floating device to permit fractionation of density gradients from the top. Anal Biochem 97:72–76, 1979

Sartory W K, Halsall H B Design of a generalized n-solute mixing-chamber gradient generator. Anal Biochem 88:539–551, 1978

McRee D Inexpensive apparatus for preparation of multiple discontinuous gradient. Anal Biochem 87:638–652, 1978

Sheeler P, Doolittle M H, White H R Method and apparatus for producing and collecting a multiplicity of density gradients. Anal Biochem 87:612–621, 1978

Michov B M A concentration gradient system. Anal Biochem 86:432–442, 1978

Corless J M Simple and inexpensive fabrication of small-volume density gradients. Anal Biochem 84:251–255, 1978

Gordon J, Ramjoue H P A simple design of an apparatus for the generation of sucrose gradients for large-scale zonal separation of ribosomal subunits. Anal Biochem 83:763–766, 1977

Gregor H D A new method for the rapid separation of cell organelles. Anal Biochem 82:255–257, 1977

Khandjian E W In situ studies of subcellular particles immobilized in sucroseacrylamide density gradients. Anal Biochem 77:387–396 1977

Allington R W, Brakke M K, Nelson J W, Aron C G, Larkins B A Optimum conditions for high-resolution gradient analysis. Anal Biochem 73:78–92, 1976

Gasser K W, DiDomenico J, Hopfer U Separation of cell organelles in density gradients based on their permeability characteristics. Anal Biochem 171:41–46, 1988

Shearer G Jr A syringe-based gradient former for linear and exponential gradients. Anal Biochem 221:397–400, 1994

Graham J, Ford T, Rickwood D The preparation of subcellular organelles from mouse liver in self-generated gradients of iodixanol. Anal Biochem 220:367–373, 1994

Ford T, Graham J, Rickwood D Iodixanol: a nonionic iso-osmotic centrifugation medium for the formation of self-generated gradients. Anal Biochem 220:360–366, 1994

Davis P B, Pearson C K Characterization of density gradients prepared by freezing and thawing a sucrose solution. Anal Biochem 91:343–349, 1978

Liedtke R, Mosebach K O An apparatus for density gradient forming and nonpuncturing fractionation. Anal Biochem 62:377–385, 1974

McCarty K S Jr, Vollmer R T, McCarty K S Improved computer program data for the resolution and fractionation of macromolecules by isokinetic sucrose density gradient sedimentation. Anal Biochem 61:165–183, 1974

Lange C S, Liberman D F A semiautomated system for the production and analysis of sucrose density gradients. Anal Biochem 59:129–145, 1974

Bylund D B, Bruening G Prediction of centrifugation times for equilibrium and velocity sedimentation on various gradients. Anal Biochem 58:47–56, 1974

Sinclair J H Churchill L, Banker G, Cotman C W Gradient design to optimize rate zonal separations. Anal Biochem 56:370–382, 1973.

Hopkins T R Another density gradient fractionator. Anal Biochem 53:339–341, 1973

Atherton R S, Hawtin P, Hutchinson P Chromatography and zonal centrifugation. Prediction of the optimum initial chamber compositions of a multichambered concentration and density gradient device. Anal Biochem 49:326–335, 1972

Dingman C W A convenient program for the rapid calculation of sedimentation coefficients in linear salt or sucrose gradients. Anal Biochem 49:124–133, 1972

Leifer W, Kreuzer T Experiments and theoretical calculations for forming gradients for zonal rotor centrifugation. Anal Biochem 44:89–96, 1971

Siakotos A N, Pennington K, McInnes A New loading system for preparing density gradients for swinging-bucket rotors using programmed gradient pumps. Anal Biochem 43:32–41, 1971

Neff S H, Meeker G L A modified fixed-volume mixer for extended sucrose density gradients. Anal Biochem 41:365–371, 1971

Pretlow T G Estimation of experimental conditions that permit cell separations by velocity sedimentation on isokinetic gradients of Ficoll in tissue culture medium. Anal Biochem 41:248–255, 1971

Wallach D F A simple system for rapid generation of duplicate density gradients. Anal Biochem 37:138–141, 1970

Shore S L, Phillips D J, Reimer C B Preformed frozen sucrose gradients—a new laboratory aid. Anal Biochem 31:114–117, 1969

Margolis J A versatile gradient-generating-device. Anal Biochem 27:319–322, 1969

Henderson A R A constant-volume device for preparing isokinetic sucrose density gradients. Anal Biochem 27:315–318, 1969.

Leif R C Density gradient system. II. A 50 channel programmable undulating diaphragm peristaltic pump. Anal Biochem 25:283–296, 1968

Leif R C Density gradient system. I. Formation and fractionation of density gradients. Anal Biochem 25:271–282, 1968

Ayad S R, Bonsall R W, Hunt S A simple method for the production of accurate linear gradients using a constant-speed peristaltic pump. Anal Biochem 22:533–535, 1968.

Mach O, Lacko L Density gradient in a dextran medium. Anal Biochem 22:393–397, 1968

McCarty K S, Stafford D, Brown O Resolution and fractionation of macromolecules by isokinetic sucrose density gradient sedimentation. Anal Biochem 24:314–329, 1968

Birnie G D, Harvey D R A simple density-gradient engine for loading large-capacity zonal ultracentrifuge rotors. Anal Biochem 22:171–174, 1968

Anderson N G, Rutenberg E Analytical techniques for cell fractions. VII. A simple gradient-forming apparatus. Anal Biochem 21:259–265, 1967

Candler E L, Nunley C E, Anderson N G Analytical techniques for cell fractions. VI. Multiple gradient-distributing rotor (B-XXI). Anal Biochem 21:253–258, 1967

McEwen C R Tables for estimating sedimentation through linear concentration gradients of sucrose solution. Anal Biochem 20:114–149, 1967

Gropper L, Griffith O Band-forming caps for the layering of sample in swinging-bucket rotors. Anal Biochem 16:171–176, 1966

Samis H V Jr A simple density gradient generator. Anal Biochem 15:355–357, 1966

Camacho-Vanegas O, Loreni F, Amaldi F. Flat absorbance background for sucrose gradients. Anal Biochem 228:172–173, 1995.

Smith G D, Osterloh K R, Peters T J Computational analysis of density gradient distribution profiles. Anal Biochem 160:17–23, 1987

Morand J N, Kent C A one-step technique for the subcellular fractionation of total cell homogenates. Anal Biochem 159:157–162, 1986

Coombs D H, Watts N R Generating sucrose gradients in three minutes by tilted tube rotation. Anal Biochem 148:254–259, 1985.

Samuels S., A continuous density gradient apparatus for use in zonal ultracentrifuges. Anal Biochem 41:164–167, 1964.

What is claimed is:

1. A method for removing zones from a density gradient having a plurality of zones therein, the method comprising the steps of:

forming a density gradient in a vessel;

applying sample particles to the gradient;

centrifuging to separate the particles into one or more zones in the gradient;

inserting a float into the vessel, the float having a concave upper surface, the concave upper surface defining a well for capturing a zone of the density gradient;

pushing the float downward into the vessel such that at least a portion of one zone of the density gradient spills over an upper circumferential edge of the float into the well; and removing the captured zone from the well.

2. A method as set forth in claim 1, wherein:

said pushing step includes using a pipette to contact and push the float downward; and said removing step includes applying suction to the pipette to remove the captured zone from the well.

3. A method as set forth in claim 1, further comprising the steps of:

pushing the float downward into the vessel such that at least a portion of a second zone of the density gradient spills over an upper circumferential edge of the float into the well; and removing the captured second zone from the well.

4. A method as set forth in claim 1, wherein:

said pushing step in claim 1 includes using a pipette to contact and push the float downward; and said removing step in claim 1 includes applying suction to the pipette to remove the second captured zone from the well.

* * * * *